United States Patent
Solem (10) Patent No.: US 6,676,695 B2
(45) Date of Patent: Jan. 13, 2004

(54) VASCULAR INSTRUMENT AND METHOD

(76) Inventor: Jan Otto Solem, Wallenruttistrasse 14, CH-8234 Stetten (CH)

(*) Notice: Subject to any disclaimer, the term of this patent is extended or adjusted under 35 U.S.C. 154(b) by 39 days.

(21) Appl. No.: 09/881,759

(22) Filed: Jun. 18, 2001

(65) Prior Publication Data

US 2002/0183825 A1 Dec. 5, 2002

(30) Foreign Application Priority Data

May 30, 2001 (SE) .............................. 0101887

(51) Int. Cl.$^7$ ................................. A61F 2/06
(52) U.S. Cl. ................ 623/1.12; 623/1.23; 606/108
(58) Field of Search ................... 623/1.11, 1.12, 623/1.23, 2.11, 108; 606/108, 153

(56) References Cited

U.S. PATENT DOCUMENTS

| | | | |
|---|---|---|---|
| 4,168,708 A | | 9/1979 | Lepley, Jr. et al. |
| 4,946,463 A | | 8/1990 | Wright |
| 5,405,378 A | * | 4/1995 | Strecker ............. 623/1.12 |
| 5,925,054 A | * | 7/1999 | Taylor et al. ........... 606/153 |
| 6,004,341 A | * | 12/1999 | Zhu et al. ............. 606/198 |
| 6,030,395 A | * | 2/2000 | Nash et al. ............ 606/153 |
| 6,110,188 A | * | 8/2000 | Narciso, Jr. ........... 606/153 |
| 2002/0033180 A1 | * | 3/2002 | Solem ................. 128/898 |

FOREIGN PATENT DOCUMENTS

WO   WO 01/13820   3/2001

* cited by examiner

Primary Examiner—Corrine McDermott
Assistant Examiner—Thomas J Sweet
(74) Attorney, Agent, or Firm—Browdy and Neimark, P.L.L.C.

(57) ABSTRACT

An instrument for introducing a vascular aid into a vessel during surgery comprises two L-shaped elements, first releasable means for locking the two L-shaped elements so as to form a T-shaped element having a stem and two oppositely directed arms, and second releasable means for connecting said vascular aid along said arms. The free ends of the arms each have a notch and the second releasable means comprises a thread to be passed through each of said notches and around said vascular aid and the adjacent arm. As a result, the vascular aid may be introduced into the vessel through a longitudinal incision therein. The first and second releasable means may then be released and the two L-shaped elements may be retracted from the vessel. A method of introducing an elongate vascular aid into a vessel through a longitudinal incision made therein during surgery comprises the steps of inserting the vascular aid through the incision into the vessel using the stem as a holder, and releasing the vascular aid from the T-shaped element to allow the vascular aid to remain within the vessel. Finally, the L-shaped elements are released from each other and are removed separately from the vessel.

32 Claims, 9 Drawing Sheets

VASCULAR INSTRUMENT AND METHOD

TECHNICAL FIELD OF THE INVENTION

The present invention relates generally to the field of vascular surgery and, more specifically, to an instrument for introducing a vascular aid, such as a vascular prosthesis or implant, into a vessel, e.g. the artery, during surgery.

BACKGROUND ART

The international patent application WO 01/13820 discloses such an instrument having two L-shaped elements, first releasable means for locking the two L-shaped elements together so as to form a T-shaped element having a stem and two oppositely directed arms, and second releasable means for connecting the arms of the T-shaped elements along a graft. The second releasable means is a suture encircling at least part of the graft and the arms of the T-shaped element.

Further, the second releasable means comprises an edge for cutting the suture. More precisely, the second releasable means comprises a needle having an edged hole at a tip thereof, through which hole the suture is extended.

Preferably, the T-shaped element has a longitudinal channel in which the needle is positioned. Further, the needle is retractable from the longitudinal channel of the T-shaped element and may have a cap enclosing the free end of the stem in its non-retracted position. Then, the needle and the cap lock the two L-shaped elements to each other.

When releasing the graft the needle is translated in its longitudinal direction, preferably retracted from the stem of the T-shaped element, whereby the edged hole in the tip of the needle cuts the suture extending through that hole. This cutting of the suture releases the graft from the oppositely directed arms of the T-shaped element. By completely removing the needle from the stem of the T-shaped element and also removing the cap, the two L-shaped elements will be released from each other. Finally, the two L-shaped elements may be withdrawn from within the vessel consecutively, leaving the graft in an appropriate position within the vessel.

According to prior art the suture is made to make a turn around the graft close to the tip or free end of each of the oppositely directed arms of the T-shaped element. In order to ensure such a turn each of the oppositely directed arms has a through hole close to its tip and the suture is made to follow a path through that hole. However, when cutting the suture the release may be obstructed by the suture sticking to the through hole.

SUMMARY OF THE INVENTION

A first object of the present invention is to further improve an instrument of the above-described type and especially enable its use for introducing a vascular aid into a vessel during surgery.

It is a further object of this invention to provide such an instrument which enables the introduction of such vascular aids as a vascular prosthesis, a vascular implant, a graft connector, a covered stent, a stented graft, a flow occluder and a flow shunt. Vascular aid is used herein as a generic term for these and similar aids.

The instrument may comprise two L-shaped elements, first releasable means for locking the two L-shaped elements so as to form a T-shaped element having a stem and two oppositely directed arms, and second releasable means for connecting the vascular aid along the arms. The free ends of the arms should each have a notch and the second releasable means may comprise a thread to be passed through each of said notches and around said vascular aid and the adjacent arm. As a result, the vascular aid may be introduced into the vessel through a longitudinal incision made therein, said first and second releasable means may be released and said two L-shaped elements may be retracted separately from the vessel.

In a first embodiment, the instrument may be adapted to introduce an elongate vascular aid selected from the group consisting of a graft connector, a covered stent and a stented graft, which vascular aid comprises a sleeve that is to be introduced into the vessel through a longitudinal incision made therein, wherein said thread is tightened around said sleeve so as to keep it compressed during the introduction into the vessel through the longitudinal incision made therein.

Specifically, the graft connector may have a collar projecting radially from the sleeve so as to form a T-shaped tube for connecting a further vessel to the incised vessel. Here, a further thread may be tightened around the collar so as to keep it compressed during the introduction and the thread may be released when the collar has been introduced into an open end of the further vessel. A graft connector of this type is disclosed in e.g. WO 01/13820.

In a second embodiment, the instrument may be adapted to introduce a flow occluder having a bar to be fixed along said arms and introduced into the vessel through a longitudinal incision made therein, said bar having ends capable of blocking flow through said vessel.

In a third embodiment, the instrument may be adapted to introduce a flow shunt having a tube to be fixed along said arms and introduced into the vessel through a longitudinal incision made therein, said tube having open ends so as to allow a flow through said vessel via said tube.

In a fourth embodiment, the instrument may be adapted to introduce a graft connector, which comprises a sleeve that is to be introduced into an open end of each of two opposing vessels, wherein said thread is tightened around said sleeve so as to keep it compressed during the introduction into the open ends of the two vessels, whereafter the first and second releasable means may be released and each of the two L-shaped elements may be retracted from its corresponding vessel.

Preferably, one of said arms is longer than the other one. Then, the longer arm is first introduced into the longitudinal incision in the vessel, whereby the length of the incision does not need to be substantially longer than the length of the shorter arm.

The first releasable means may comprise a cap for enclosing part of said stem and the second releasable means may comprise an edge for cutting said thread.

In a preferred embodiment, the second releasable means comprises a needle having an edged hole at a tip thereof and the cap enclosing the free end of the stem. Also, the two L-shaped elements may form a longitudinal channel for receiving the needle, which is retractable from this channel and which in its non-retracted position locks the two L-shaped elements to each other together with the cap.

According to a second aspect of the invention, an instrument for introducing an elongate vascular aid into a vessel during surgery comprises an L-shaped element having a stem and an arm, and a releasable means for connecting the vascular aid along the arm, whereby the vascular aid may be introduced into the vessel through the open end thereof, said releasable means may be released and said L-shaped element may be withdrawn from the vessel.

According to a further aspect of the invention, a method of introducing an elongate vascular aid into a vessel through a longitudinal incision made therein during surgery comprises the steps of providing two L-shaped elements, locking the two L-shaped elements releasably to each other so as to form a T-shaped element having a stem and two oppositely directed arms each having a notch at a free end thereof, positioning the vascular aid along the arms, passing a thread through the notches and encircling the sleeve and the arms for locking the vascular aid to the arms, inserting the vascular aid through the incision into the vessel using the stem as a holder, releasing the vascular aid from the T-shaped element to allow the vascular aid to remain within the vessel, releasing the L-shaped elements from each other, and retracting the L-shaped elements from the vessel.

The diameter of the elongate vascular aid may be reduced by the releasable locking thereof along the arms of the T-shaped element. Preferably, the vascular aid is released from the T-shaped element by cutting the thread.

According to still another aspect of the invention, a method of introducing an elongate vascular aid into an open end of each of two opposing vessels during surgery comprises the steps of providing two L-shaped elements, locking the two L-shaped elements releasably to each other so as to form a T-shaped element having a stem and two oppositely directed arms each having a notch at a free end thereof, positioning the vascular aid along the arms, passing a thread through the notches and encircling the sleeve and the arms for locking the vascular aid to the arms, inserting the vascular aid into the open ends of the two vessels using the stem as a holder, releasing the vascular aid from the T-shaped element to allow the vascular aid to remain within the two vessels, releasing the L-shaped elements from each other, and retracting the L-shaped elements from the vessels.

BRIEF DESCRIPTION OF THE DRAWINGS

The invention will now be described in more detail with reference to the accompanying drawings, in which.

DETAILED DESCRIPTION OF PREFERRED EMBODIMENTS OF THE INVENTION

Figure 1:
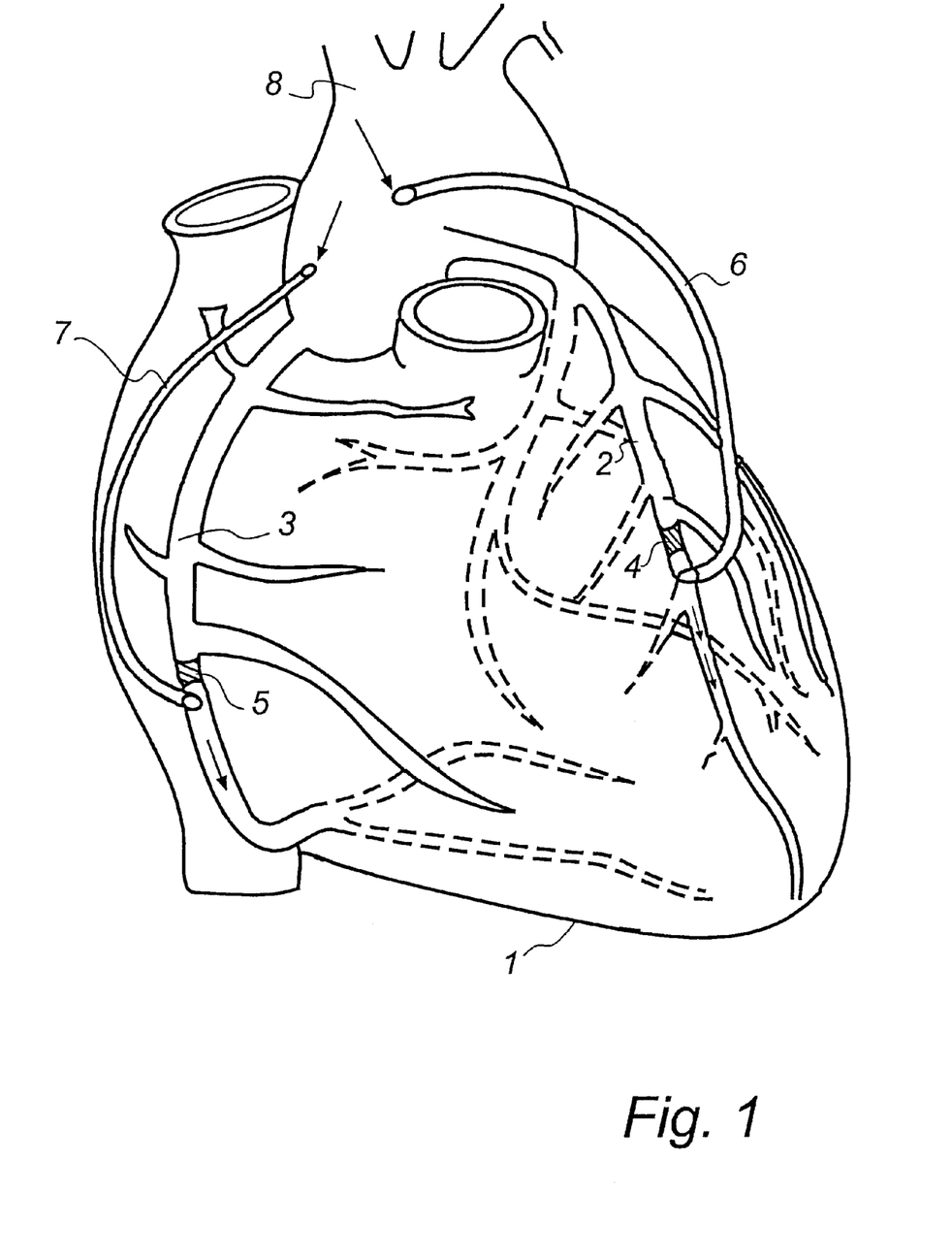
FIG. 1 is a perspective view and shows a heart with two schematically indicated bypasses of a coronary vessel each having a blocking.

The heart 1 shown in FIG. 1 has two coronary vessels 2, 3 each having a blocking 4, 5, i.e. a stenosis or an occlusion. FIG. 1 illustrates schematically how these blockings 4, 5 are bypassed by means of two grafts or vessels 6, 7 which can be taken from the patient himself. More specifically, one end of the vessel 6 is connected after the blocking 4, seen in the normal direction of flow in the vessel 2, and its other end is connected to the aorta 8, such that a sufficient quantity of oxygen-rich blood will be supplied to the already blocked coronary vessel 2 after the blocking 4 therein. The same applies to the vessel 3.

Figure 2:
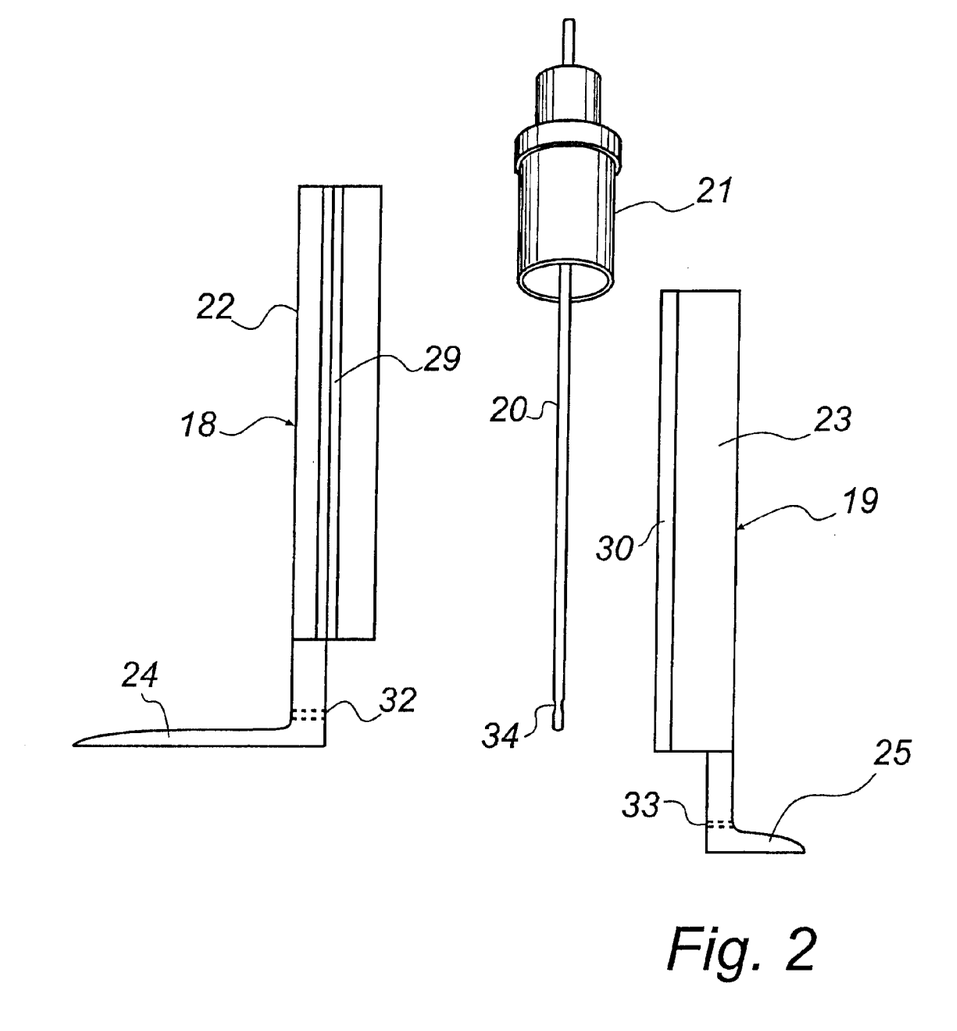
FIG. 2 is a perspective view and shows an embodiment of an introducer instrument according to the present invention.
Figure 3:
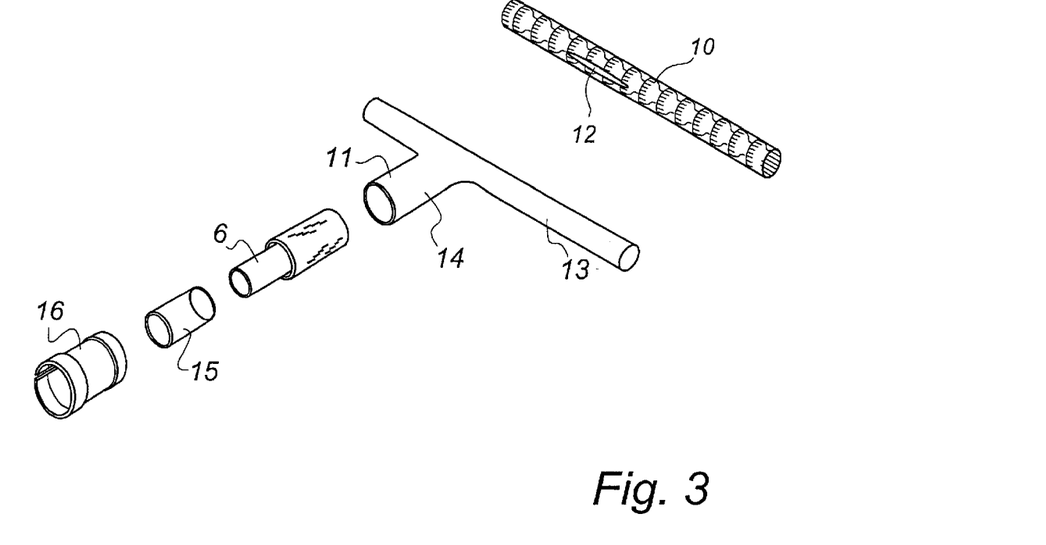
FIG. 3 is a perspective view and shows, among other things, a few parts included in a graft connector to be introduced by the instrument according to the invention.
Figure 4:
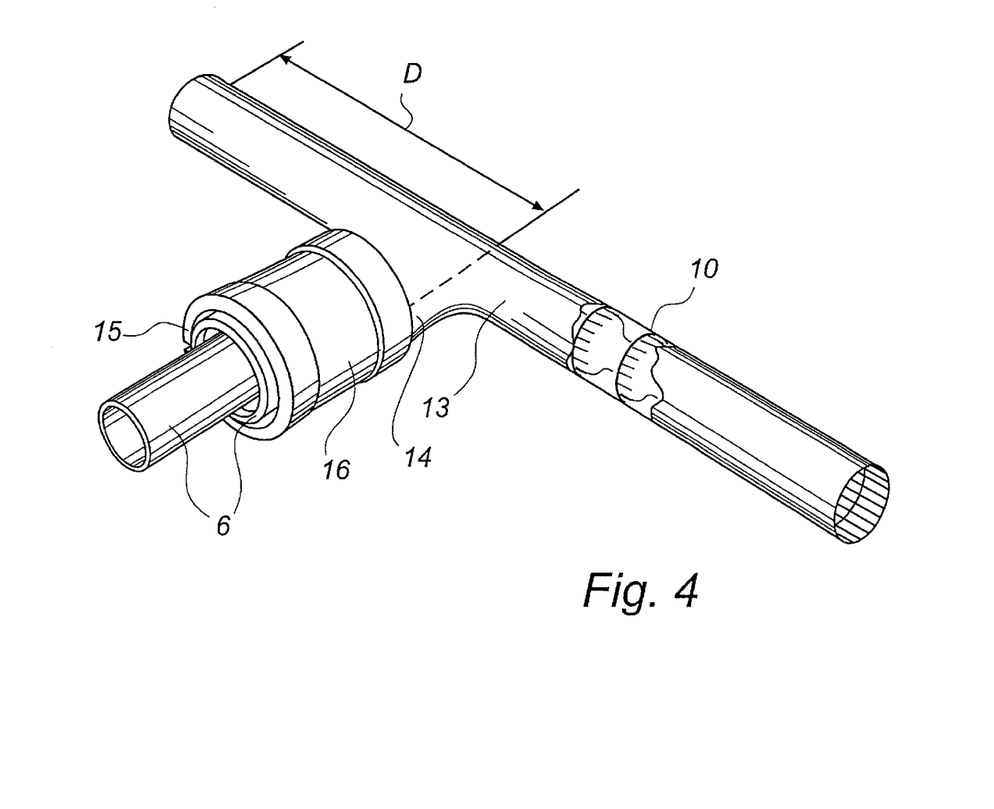
FIG. 4 shows the parts in FIG. 3 in an assembled state before insertion into a blocked vessel.

For effecting the connection of the vessel 6 to the coronary vessel 2, an instrument as shown in FIG. 2 may be used for the introduction of a graft connector or branching device shown in FIGS. 3 and 4.

The main components of the graft connector are a sleeve 10 and a collar 11 fixed thereto. The sleeve 10 preferably consists of a memory material that is not rejected by the body tissue. Its construction is such as to have a predetermined diameter, which can be reduced by compression. When releasing the compression, the sleeve 10 will automatically expand to its predetermined, larger diameter.

A suitable material for the sleeve 10 is in the form of a net that permits said compression and expansion.

Further, the sleeve 10 has an axially elongate opening 12, whose dimensions, when the sleeve 10 expands, may be distorted in a manner similar to the distortion of the actual sleeve 10, i.e. a shortening in the axial direction and an expansion in the circumferential direction. The opening 12 may thus obtain a decreased length in the axial direction of the sleeve 10, but an increased width in the circumferential direction of the sleeve 10.

The collar 11 consists of a fluid-tight and preferably flexible or even elastic material, which of course must also be such as not to risk being rejected by the body tissue. More specifically, the collar 11 has a shoulder portion 13 and a neck portion 14.

The shoulder portion 13 has a shape substantially conforming to the shape of the sleeve 10. It has such a size as to overlap the opening 12 and thus extend over the sleeve 10 around the opening 12. The overlapping is also so great as to remain also in case of a certain change of the size of the opening 12, as will be described below. The shoulder portion 13 can also completely encompass at least part of or the entire sleeve 10, in which case the material of the shoulder portion 13 is so elastic as not to essentially counteract a compression or The expansion of the sleeve 10, as will be described below. Preferably, the shoulder portion 13 completely encompasses the entire sleeve 10, as shown in FIG. 4.

The neck portion 14 of the collar 11 is a direct extension of the shoulder portion 13 and essentially has the shape of a cylinder. The most important function of the neck portion 14 is to serve as a connecting member for the graft or new vessel 6.

For the connection between the neck portion 14 and the vessel 6, a rigid supporting sleeve 15 and a clamping or locking sleeve 16 can be used according to the embodiment illustrated in FIGS. 3 and 4 of the drawings. The end of the vessel 6 is adapted to be inserted into and through the supporting sleeve 15, and the outermost part of the vessel 6 is then to be folded or pulled back over the outside of the supporting sleeve 15. This folding back of the end of the vessel 6 is shown in FIG. 3, but with the supporting sleeve 15 separated from the vessel 6. For completion of the connection, the supporting sleeve 15 with the pulled-on vessel 6 is inserted into the open end of the neck portion 14. Then the clamping sleeve 16 is arranged and clamped around the neck portion 14, which then together with the interiorly situated, folded-back part of the vessel 6 is pressed against the outside of the supporting sleeve 15. As a result, a fixed and tight connection between the neck portion 14 and the vessel 6 is achieved.

The actual clamping sleeve 16 may be divisible so as to be laterally movable over the neck portion 14 before the clamping operation, which suitably is effected by the clamping sleeve 16 having, at its ends that are free before clamping, hooks engaging each other and permitting easy tightening of the clamping sleeve 16 around the neck portion 14.

For fixing the sleeve 10 and the collar 11 relative to e.g. the blood vessel 2 in FIG. 1, the sleeve 10 is made of a memory material and removable means are used for temporarily reducing the diameter of the sleeve 10 during insertion into the blood vessel 2. By releasing these removable means, the sleeve 10 can be expanded in its place within the blood vessel 2, such that the blood vessel 2 also is expanded and thus is pressed against the sleeve 10 for fixing the position thereof in the blood vessel 2. At the same time the collar 11, more precisely the shoulder portion 13, will be squeezed between the blood vessel 2 and the sleeve 10, such that the position of the collar 11 will be safely fixed relative to the blood vessel 2 and a fluid-tight seal between this vessel 2 and the collar 11 is obtained without necessitating any suture.

It is preferable to first prepare the connection between the collar 11 and the new vessel 6. Subsequently, the sleeve 10 can in a reciprocating movement be inserted into, for instance, the vessel 2 through the opening formed therein by a longitudinal incision. Then the branching device is fixed in the vessel 2 by release of the removable means, whereby the sleeve 10 expands.

For completion of the operation, the free end of the new vessel 6 is to be connected to a blood vessel, for instance the aorta 8, which can give a sufficient flow of blood to the vessel 2 after the blocking 4.

In an alternative method of carrying out a bypass operation by means of the graft connector, the new vessel 6 is first connected to the blood vessel, e.g. the aorta, which can give a sufficient flow of blood, and is then connected to the vessel having a blocking.

According to a further alternative, an arterial vessel originating from the aorta or some other artery, e.g. the internal mammary artery, capable of giving a sufficient flow of blood may be used as the new vessel 6, thus requiring connection only at one end.

It should be emphasised that in the methods described above, the collar 11 is even from the beginning fixed to the sleeve 10, and that the shoulder portion 13 preferably encompasses the entire sleeve 10.

FIG. 2 shows elements 18–21 of an introducer or inserter. These elements 18–21 include two L-shaped elements 18 and 19, a tubular needle 20 and a cap 21. The L-shaped elements 18 and 19 each have a stem portion 22 and 23, respectively, and the arm 24 and 25, respectively. The arms 24 and 25 are of different length, the arm 24 being longer than the arm 25. This difference in length corresponds to the asymmetric position of the opening 12 in the sleeve 10. At least one of the arms 24 and 25 may also be curved to fit into tortuous vessels.

Figure 5:
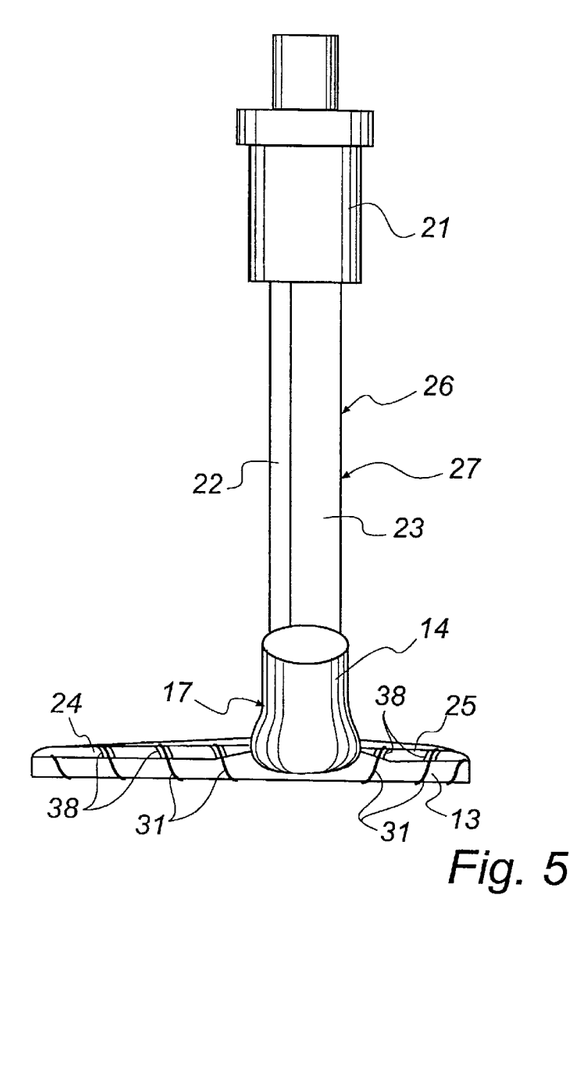
FIG. 5 is a front view and shows the introducer of FIG. 2 and the graft connector of FIG. 4 in an assembled state before insertion into a blocked vessel.
Figure 6:
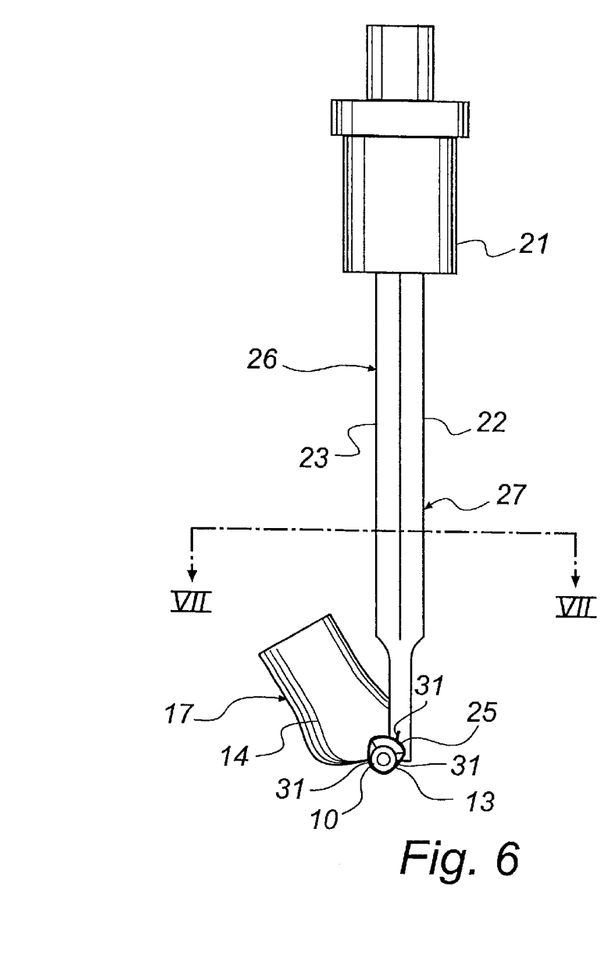
FIG. 6 is a side view of the introducer and the graft connector in FIG. 5.

The two L-shaped elements 18 and 19 may be assembled so as to form a T-shaped element 26 having a stem 27 formed by the two stem portions 22 and 23, as illustrated in FIGS. 5 and 6, and the arms 24 and 25 extending in opposite directions. The two L-shaped elements 18 and 19 may be locked in the assembled state by means of the cap 21 and the needle 20.

The locking effect of the cap 21 is obtained when the cap 21 is pushed down on the free end of the stem 27, thereby blocking the corresponding ends of the stem portions 22 and 23 from moving away from each other.

Figure 7:
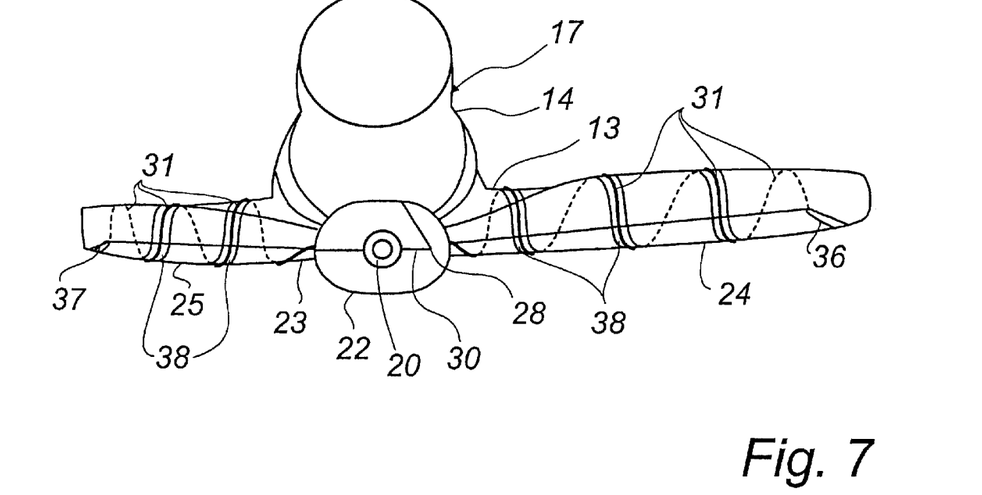
FIG. 7 is a top view, partly in cross-section along the lines VII—VII in FIG. 6, FIG. 8 a cross-sectional view through the tip of a needle and partly through arms shown in FIG. 2 and illustrates the means for connecting the introducer to the graft connector.

The locking effect of the needle 20 follows from the cross-sectional shape of the stem portions 22 and 23, as illustrated in FIG. 7. The stem portion 22 has a V-shaped cut 28, and the stem portion 23 has a cross-sectional shape that is complementary to the cross-sectional shape of the cut 28. A longitudinal channel 29 of circular cross-sectional shape is formed partly in the stem portion 22 and partly in the stem portion 23 so that an edge 30 of the stem portion 23 is locked in the inner corner of the cut 28, when the needle 20 is inserted into the channel 29.

In order to be able to insert the sleeve 10 into a blood vessel, in which an opening of substantially the same length as the length D in FIG. 4 is made by an incision, the sleeve 10 has to be compressed temporarily during the insertion. This compression is obtained by removable means, such as a thread encircling at least part of the sleeve 10 as well as the encompassing shoulder portion 13. In its compressed state, the sleeve 10 can be introduced through the incised opening in the blood vessel by a reciprocating movement leaving the neck portion 14 close to one end of the longitudinal opening in the blood vessel.

According to the present invention, the introducer or inserter is preferably used for the above-described introducing of the sleeve 10 into the blood vessel in which a longitudinal incision has been made. More precisely, the L-shaped elements 18 and 19 are assembled as described above to form the T-shaped element 26 and then the sleeve 10 is compressed and connected along the arms 24 and 25 of the T-shaped element 26. This connection is made by second releasable means such that the arms 24 and 25 may be released from the sleeve 10 when the sleeve 10 is inserted into the blood vessel and correctly positioned therein. The compression of the sleeve 10 should preferably be suspended substantially at the same time, such that the sleeve 10 expands and assumes a fixed position in the blood vessel.

When the arms 24 and 25 are released from the sleeve 10, they may be released from each other. They are then easily removed from the blood vessel one at a time.

Figure 8:
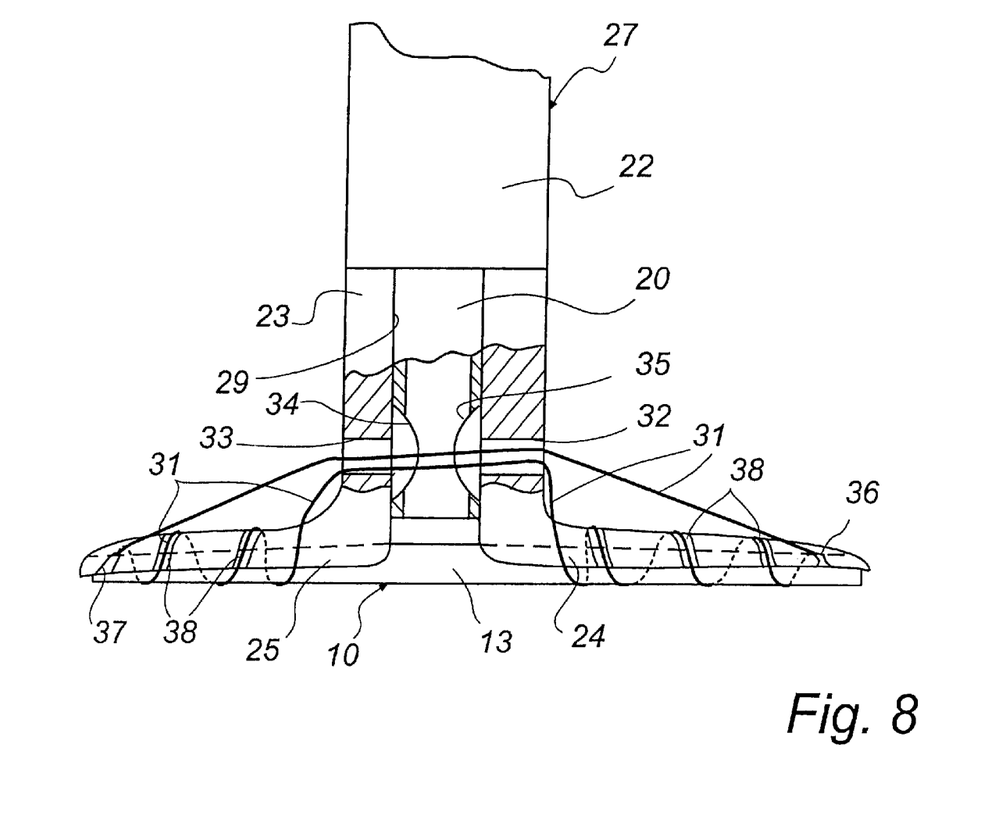

The compression of the sleeve 10 and the encompassing shoulder portion 13 may be made by a suture thread 31, preferably of polypropylene shown in FIGS. 7 and 8. This thread 31 is wound around the sleeve 10 and the shoulder portion 13 so as to encircle at least part thereof and thereby reduce the diameter of the sleeve 10. Further, it is advantageous to use the same thread 31 for connecting the sleeve 10 to the arms 24 and 25, such that by cutting the thread 31 by means of an edge means the arms 24 and 25 will be released from the sleeve 10 and the memory material of the sleeve 10 will be allowed to expand the sleeve 10 to the predetermined diameter.

The needle 20 is used for cutting the thread 31. More precisely, the thread 31 is guided through holes 32 and 33 extending through the stem portions 22 and 23 close to the arms 24 and 25. The needle 20 has corresponding holes 34 at its tip receiving the thread 31, which extends, preferably twice, between the holes 32 and 33. The holes 34 are edged, each having a sharp edge 35, such that when the needle 20 is moved out from the channel 29 in the stem 27, the thread 31 will be cut. The thread 31 would also be cut by a twisting movement of the needle 20 in the channel 29 in the stem 27.

As shown in FIGS. 7 and 8, the arms 24 and 25 each have a notch 36 and 37, respectively, near the tip thereof. The notch 36 has a mouth pointing away from the stem 22, and the notch 37 has a mouth pointing away from the stem 23. Alternatively, the tips of the arms 24 and 25 may be bifurcated so as to form notches. The notches 36, 37 are used to ensure that the thread 31 makes at least one turn around the sleeve 10 close to the tip of each of the arms 24 and 25, and consequently close to the ends of the sleeve 10. More precisely, the thread 31 may follow a path from the hole 32 around the compressed sleeve 10 and the arm 24 in one or several turns to the notch 36 at the tip of the arm 24, through this notch 36, and back to and through the hole 32 in the stem portion 22. The thread 31 then passes through the hole 34 in the needle 20 and the hole 33 in the stem portion 23, around the compressed sleeve 10 and the arm 25 in one or several turns to the notch 37 at the tip of the arm 25, through this notch 37, and back to and through the hole 33 in the stem portion 23 and the hole 34 in the needle 20.

As a result, the thread 31 forms an endless loop connecting the arms 24, 25 of the T-shaped element 26 to the sleeve 10 and also compressing the sleeve 10.

As best shown in FIG. 7, the arms 24 and 25 may have grooves 38, which are inclined towards the longitudinal direction of the arms 24 and 25 for controlling the position of the loops of the thread 31 therearound.

It should be noted that the thread 31 may be guided along other paths through the holes 32, 33, 34 and the notches 36 and 37.

The thread 31 represents a first embodiment of removable means for temporarily reducing the diameter of the sleeve during insertion into a blood vessel. The thread 31 also constitutes second releasable means for connecting the arms of the T-shaped element 26 along the sleeve 13 of the graft connector. Of course, separate threads could be used as said removable means and said second releasable means.

Figure 9:
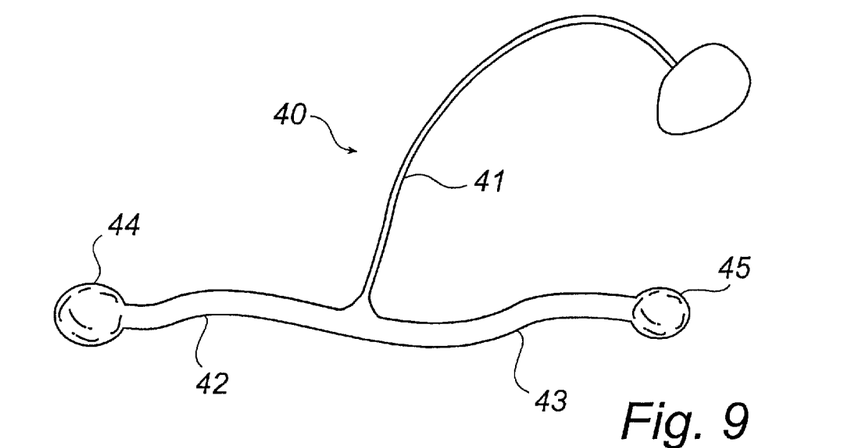
FIG. 9 is a perspective view of a flow occluder to be introduced by an instrument according to the invention.

Another elongate surgical vascular aid is shown in FIG. 9. This vascular aid is a flow occluder 40 having a stem 41 and two opposing arms 42, 43 forming a bar at one end of the stem 41. The free ends of the arms 42, 43 each has a bulb 44, 45 respectively.

Figure 10:
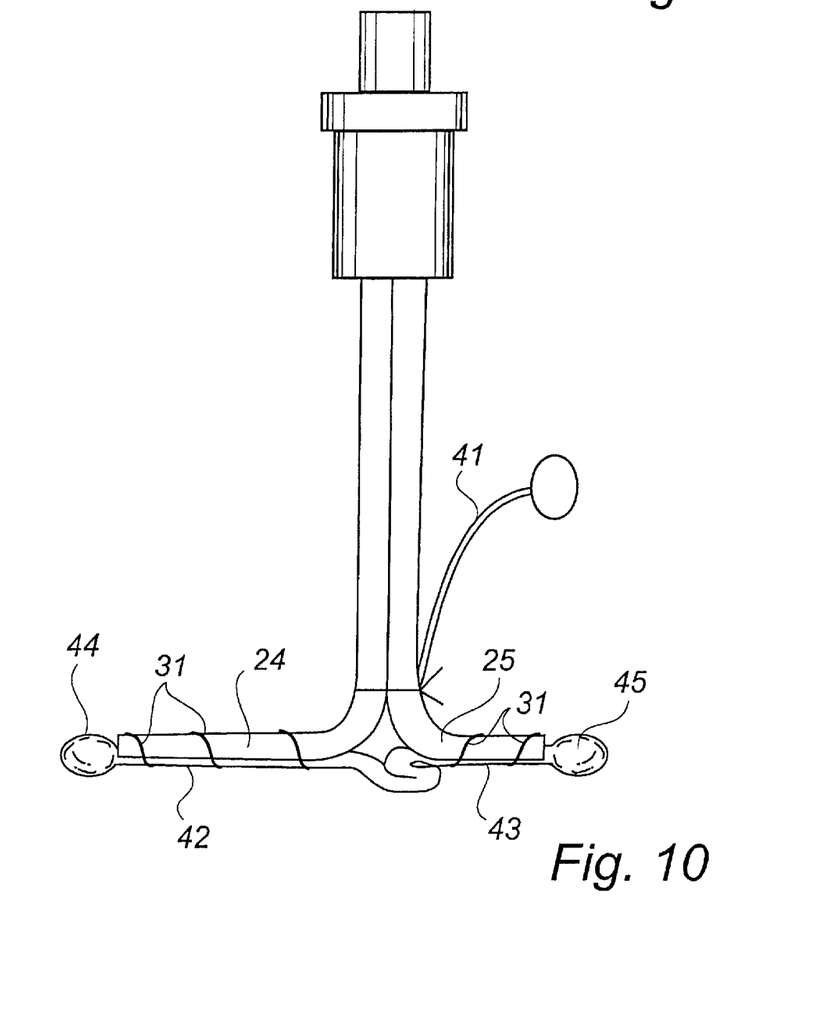
FIG. 10 is a front view corresponding to FIG. 5 and shows the introducer of FIG. 2 and the flow occluder of FIG. 9 in the assembled state before insertion into a vessel.

The flow occluder 40 may be fixed to an introducer according to the invention as shown in FIG. 10, i.e. by a thread 31 substantially in the same manner as the sleeve 10. Then the occluder 40 is insertable through an incision in a vessel with the arms 42, 43 and the bulbs 44, 45 extending in opposite directions along the vessel. As a result, a section of the blood vessel between the bulbs 44, 45 is sealed off at both ends for completion of anastomosis or other purposes.

Figures 11, 12:
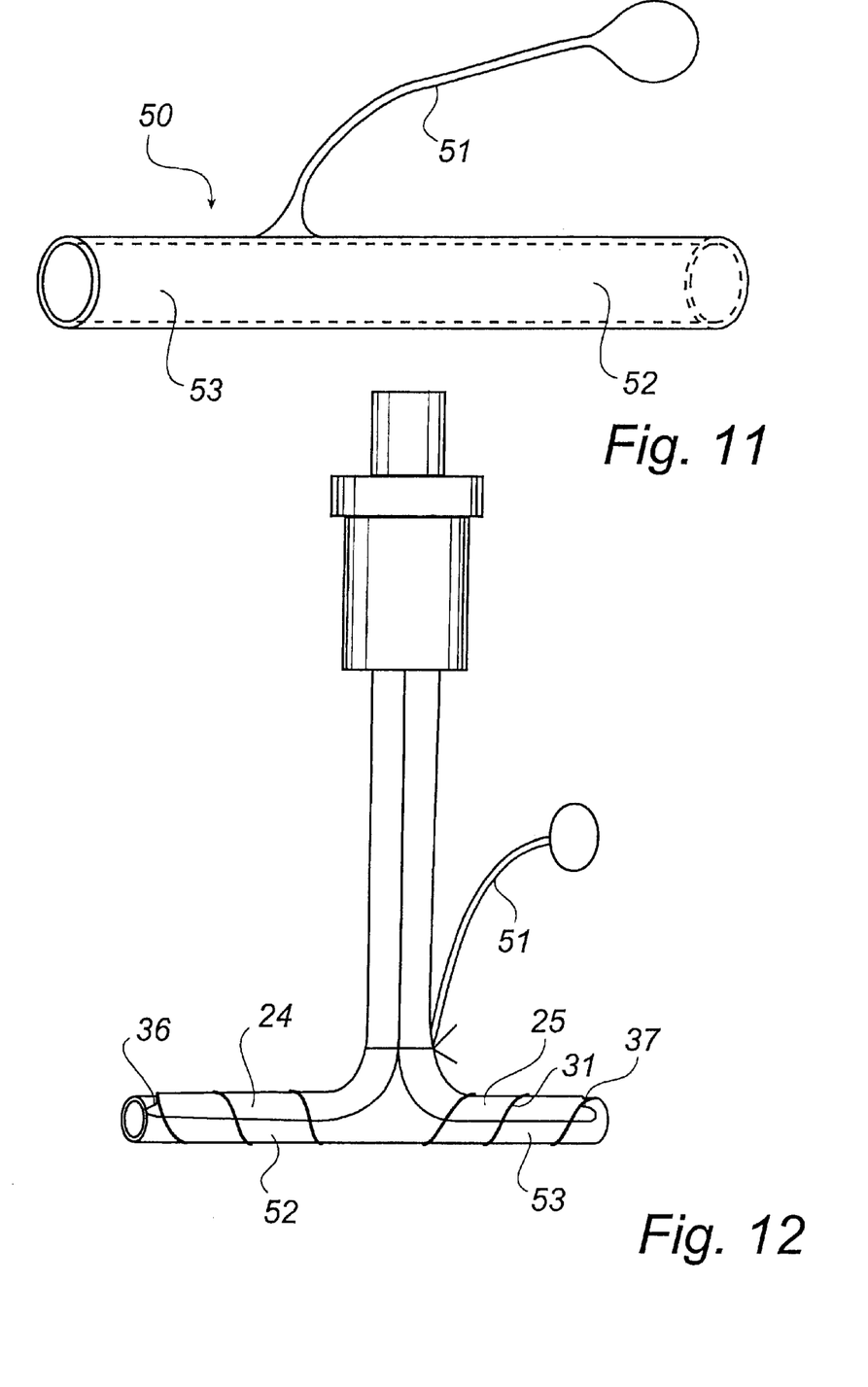
FIG. 11 is a perspective view of a flow shunt to be introduced into a vessel by an instrument according to the invention.
FIG. 12 is a front view corresponding to FIG. 5 and shows the introducer of FIG. 2 and the flow shunt of FIG. 11 in the assembled state before insertion into a vessel.

Still another elongate surgical vascular aid is shown in FIGS. 11 and 12. This vascular aid is an open-ended tube 50 having a stem 51 and two opposing arms 52 and 53 which can be fixed to the arms 24, 25 of the instrument according to the invention much in the same manner as the flow occluder 40 and the sleeve 10. The tube 50 may be used during suturing of an anastomosis in order to secure blood flow past the site of the vessel where the anastomosis is performed. The stem 51 may be attached asymmetrically on the tube 50, permitting the sections or arms 52 and 53 to have different lengths.

Figures 13, 14:
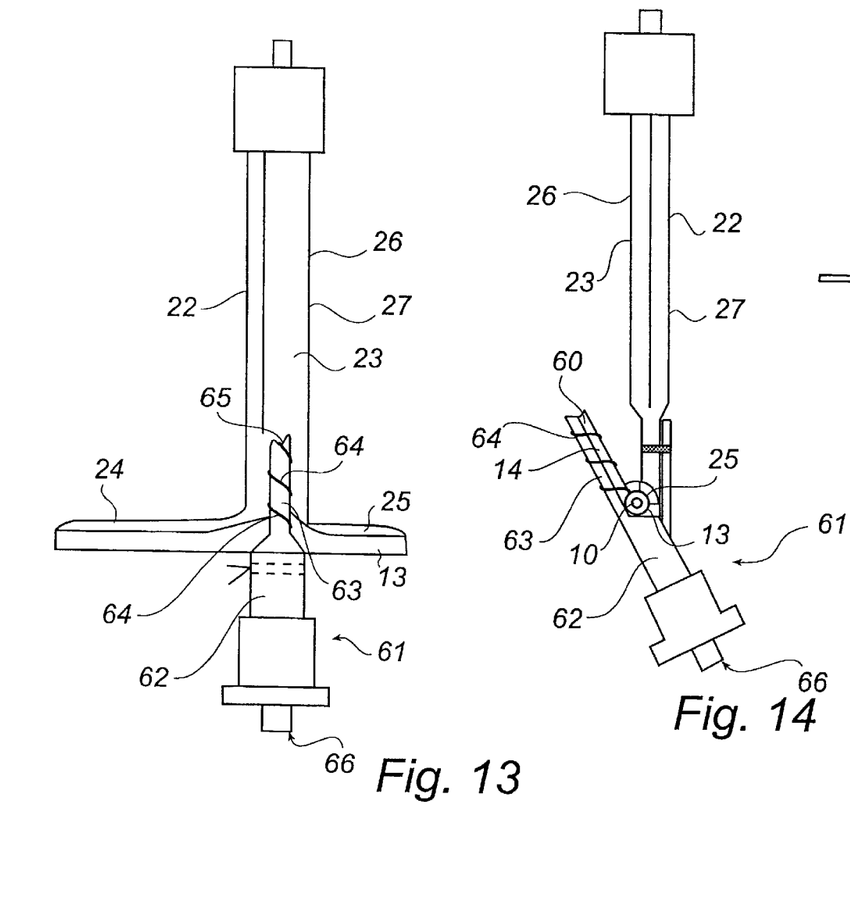
FIGS. 13 and 14 are views corresponding to FIGS. 5 and 6, respectively, and illustrate a modification of the introducer for a modified graft connector.

Still another elongated vascular aid is shown in FIGS. 13 and 14. More precisely, the vascular aid of FIGS. 13 and 14 is a graft connector which corresponds to the graft connector shown in FIGS. 3 and 4 except that the supporting sleeve 15 and the locking sleeve 16 are not used. Instead, the neck portion 14 of the collar 11 encloses a sleeve 60 of the same material as the sleeve 10. Thus, the sleeve 60 preferably consists of a memory material that is not rejected by the body tissue. Further, its construction is such as to have a predetermined diameter, which can be reduced by compression. When releasing the compression, the sleeve 60 will automatically expand to its predetermined, larger diameter. In its compressed state, the neck portion 14 should be insertable into the open end of the vessel 6. After being inserted into the vessel 6, the neck portion 14 should be allowed to expand and be fixed within the vessel 6 in its expanded state. The introducer 61 of FIGS. 13 and 14 comprises a stem 62 and an arm 63 as an extension of the stem 62. Further, the introducer 61 includes a thread 64, which is wound around the sleeve 60 and the arm 63 to keep the sleeve 60 compressed. This thread 64 is passed via a notch 65 at the free end of the arm 63. It may be released in the same way as the thread 31 by means of a further edge means, e.g. a further needle 66 received in the stem 62.

The introducer 61 need not be fixed to the stem of the introducer for the sleeve 13 but can be releasably fixed thereto by means of an extra arm and a clip, as schematically illustrated in FIG. 14.

Preferably, the neck portion 14 is first introduced into and fixed in the open-end portion of the vessel 6. Then, the sleeve 10 is introduced and fixed in its vessel as described above.

Figure 15:
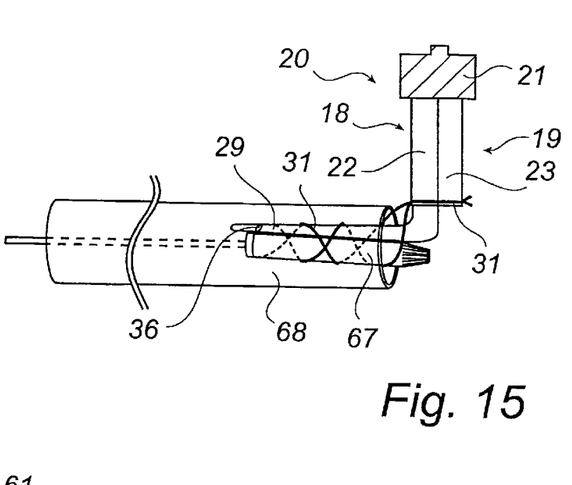
FIG. 15 illustrates a further modification of the introducer of FIG. 2, and FIGS. 16–20 illustrate several of the surgery results obtainable by the present invention.

The introducer illustrated in FIG. 15 corresponds to the introducer shown in FIG. 2 except that only one arm 25 is used. The other arm 25 is cut below the hole 33 of the stem portion 23 and eliminated. Thus, the introducer of FIG. 15 comprises the L-shaped element 18, the stem portion 23 of the L-shaped element 19, the needle 20 with the cap 21 and the thread 31, which in this case ends at the stem portion 23.

As shown in FIG. 15, a sleeve 67 may be introduced into an end of a vessel 68 for subsequently connecting this vessel 68 to a larger vessel. The sleeve 67 may be of a type illustrated in my U.S. patent application Ser. No. 09/769,748 which was filed on Jan. 26, 2001 as a CIP Application of U.S. patent application Ser. No. 09/228,749, filed on Jul. 23, 1997 and issued on Jan. 30, 2001 as U.S. Pat. No. 6,179,848. Both these documents are incorporated herein by reference.

Using the same technique, a stented vascular graft (also called covered stent or covered stent graft) with no collar 11 may also be inserted into any hollow tubular formation of the human body like the arteries, veins, biliary ducts, urinary tract and the bronchial tree.

FIGS. 16–20 are longitudinal sectional views illustrating four applications of the present invention during surgery.

Figure 16:
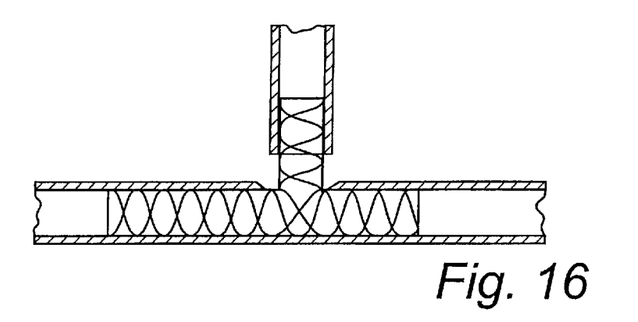

FIG. 16 shows the result of a surgery using the graft connector and the introducer illustrated in FIGS. 13 and 14.

Figure 17:
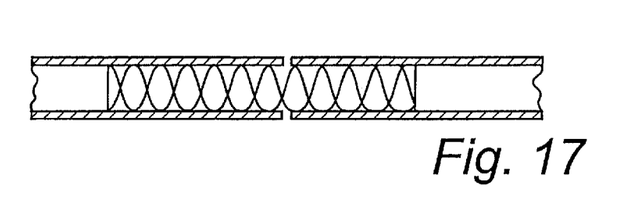

FIG. 17 shows the result of a surgery using a cylindrical stented vascular graft for connecting the open ends of two opposing vessels to each other using an introducer according to FIGS. 5–8.

Figure 18:
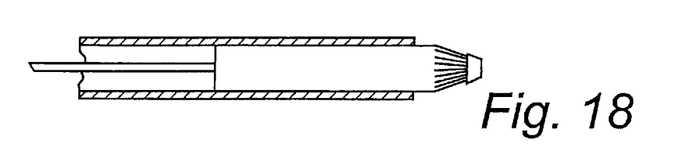

FIG. 18 shows the result of a surgery according to FIG. 15.

Figure 19:
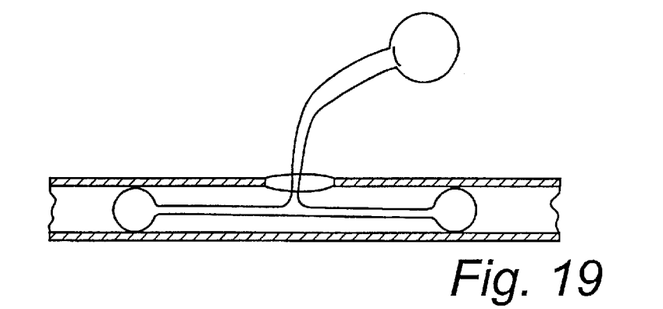

FIG. 19 shows the use of the flow occluder and the introducer shown in FIG. 10 during surgery on a vessel.

Figure 20:
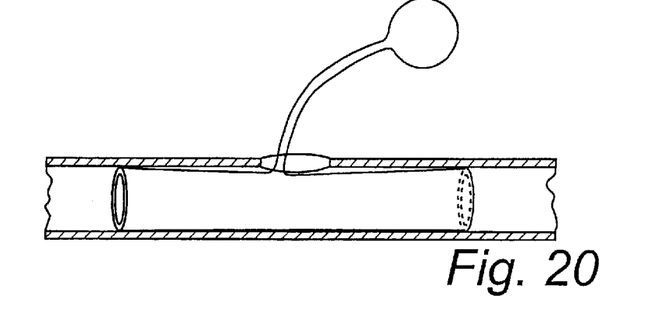

FIG. 20 illustrates the use of the introducer and the stent tube shown in FIG. 12 for bypassing the opening in a vessel.

The expert realises that several modifications of the above-described embodiments of the graft connector and the introducer or inserter are conceivable within the scope of the invention as defined in the appended claims. Thus, the invention may be used also for vessels of a relatively large diameter, e.g. for excluding the aneurysm or other local dilatation of the aorta.

What is claimed is:

1. An instrument for introducing an elongate vascular aid into a vessel during surgery, comprising
   two L-shaped elements,
   first releasable means for locking the two L-shaped elements so as to form a T-shaped element having a stem and two oppositely directed arms, and
   second releasable means for connecting said vascular aid along said arms,
   wherein the free ends of said arms each have a notch and said second releasable means comprises a thread to be passed through each of said notches and around said vascular aid and the adjacent arm.

2. The instrument as claimed in claim 1 for an elongate vascular aid selected from the group consisting of a graft connector, a covered stent and a stented graft, which vascular aid comprises a sleeve that is to be introduced into the vessel through a longitudinal incision made therein, wherein said thread is tightened around said sleeve so as to keep it compressed during the introduction through the longitudinal incision into the vessel, whereafter said first and second releasable means may be released and said two L-shaped elements may be retracted separately from the vessel.

3. The instrument as claimed in claim 2 for a graft connector having a collar projecting radially from the sleeve so as to form a T-shaped tube for connecting a further vessel to the incised vessel, wherein a further thread is tightened around the collar so as to keep it compressed during said introduction and may be released when said collar is introduced into the open end of said further vessel.

4. The instrument as claimed in claim 1 for a flow occluder having a bar to be fixed along said arms and introduced into the vessel through a longitudinal incision made therein, said bar having ends capable of blocking a flow through said vessel.

5. The instrument as claimed in claim 1 for a flow shunt having a tube to be fixed along said arms and introduced into the vessel through a longitudinal incision made therein, said tube having open ends so as to allow a flow through said vessel via said tube.

6. The instrument as claimed in claim 1 for a graft connector, which comprises a sleeve that is to be introduced into an open end of each of two opposing vessels, wherein said thread is tightened around said sleeve so as to keep it compressed during the introduction into the open ends of the two vessels, whereafter said first and second releasable means may be released and each of the two L-shaped elements may be retracted from its corresponding vessel.

7. The instrument as claimed in claim 1, wherein one of said arms is longer than the other one.

8. The instrument as claimed in claim 1, wherein each of the arms has grooves for receiving the thread passed around the vascular aid and the arms.

9. The instrument as claimed in claim 1, wherein said first releasable means comprises a cap for enclosing part of said stem.

10. The instrument as claimed in claim 1, wherein said second releasable means comprises the edge for cutting said thread.

11. The instrument as claimed in claim 10, wherein said edge comprises an edged hole at a tip of a needle.

12. The instrument as claimed in claim 11, wherein said two L-shaped elements form a longitudinal channel for receiving said needle.

13. The instrument as claimed in claim 12, wherein said needle is retractable from the longitudinal channel of the T-shaped element and has a cap enclosing the free ends of the stem in its non-retracted position.

14. The instrument as claimed in claim 13, wherein the needle and the cap lock the two L-shaped elements to each other.

15. An instrument for introducing an elongate vascular aid into a vessel during surgery, comprising
   an L-shaped element having a stem portion and an arm,
   a releasable means for connecting the vascular aid along the arm,
   wherein the releasable means comprises a thread passed around the vascular aid and the arm, and wherein the arm has grooves for receiving the thread passed around the vascular aid and the arm,
   whereby the vascular aid may be introduced into the vessel through an open end thereof, said releasable means may be released and said L-shaped element may be withdrawn from the vessel.

16. The instrument as claimed in claim 15, wherein the free end of the arm has a notch for receiving the thread passed around the vascular aid and the arm.

17. An instrument for introducing an elongate vascular aid into a vessel during surgery, comprising
   an L-shaped element having a stem portion and an arm,
   a releasable means for connecting the vascular aid along the arm,
   whereby the vascular aid may be introduced into the vessel through an open end thereof, said releasable means may be released and said L-shaped element may be withdrawn from the vessel,
   wherein the releasable means comprises a thread passed around the vascular aid and the arm, and
   wherein a second stem portion is releasably fixed along the stem portion of the L-shaped element.

18. The instrument as claimed in claim 17, wherein said releasable means comprises an edge for cutting said thread.

19. The instrument as claimed in claim 18, wherein said edge comprises an edged hole at a tip of a needle.

20. The instrument as claimed in claim 19, wherein the stem portions form a longitudinal channel for receiving the needle.

21. The instrument as claimed in claim 20, wherein the needle is retractable from the longitudinal channel and has a cap enclosing the free ends of the stem portions in its non-retracted position.

22. The instrument as claimed in claim 21, wherein the needle and the cap lock the stem portions to each other.

23. An instrument for introducing an elongate vascular aid into a vessel during surgery, comprising
   a stem and an arm as an extension of the stem, a releasable means for connecting the vascular aid along the arm, wherein the releasable means comprises a thread passed around the vascular aid and the arm, and wherein the arm has grooves for receiving the thread passed around the vascular air and the arm, whereby the vascular aid may be introduced into the vessel through an open end thereof, said releasable means may be released and said stem and said arm may be withdrawn fro the vessel.

24. The instrument as claimed in claim 23, wherein the free end of the arm has a notch for receiving the thread passed around the vascular aid and the arm.

25. An instrument for introducing an elongate vascular aid into a vessel during surgery, comprising a stem and an arm as an extension of the stem, a releasable means for connecting the vascular aid along the arm, whereby the vascular aid may be introduced into the vessel through an open end thereof, said releasable means may be released and said stem and said arm may be withdrawn fro the vessel, wherein the releasable means comprises a thread passed around the vascular aid and the arm, and wherein said releasable means comprises a needle having an edge for cutting said thread.

26. The instrument as claimed in claim 25, wherein said edge comprises an edged hole at a tip of said needle.

27. A method of introducing an elongate vascular aid into a vessel through a longitudinal incision made therein during surgery, said method comprising the steps of providing two L-shaped elements, locking the two L-shaped elements releasably to each other so as to form a T-shaped element having a stem and two oppositely directed arms each having a notch at a free end thereof, positioning the vascular aid along the arms, passing a thread through the notches and encircling the vascular aid and the arms for locking the vascular aid to the arms, inserting the vascular aid through the incision into the vessel using the stem as a holder, releasing the vascular aid from the T-shaped element to allow the vascular aid to remain within the vessel, releasing the L-shaped elements from each other, and retracting the L-shaped elements from the vessel.

28. The method as claimed in claim 27, wherein the diameter of the vascular aid is reduced by the releasable locking thereof along the arms of the T-shaped element.

29. The method as claimed in claim 27 or 28, wherein the vascular aid is released from the T-shaped element by cutting the thread.

30. The method as claimed in claim 27, wherein a vascular air having a self-expanding sleeve is used.

31. The method as claimed in claim 27, wherein a vascular aid requiring balloon expansion oft the sleeve is used.

32. The method of introducing an elongate vascular aid into the open end of each of two opposing vessels during surgery, said method comprising the steps of providing two L-shaped elements, locking the two L-shaped elements releasably to each other so as to form a T-shaped element having a stem and two oppositely directed arms each having a notch at a free end thereof, positioning the vascular aid along the arms, passing a thread through the notches and encircling the sleeve and the arms for locking the vascular aid to the arms, inserting the vascular aid into the open ends of the two vessels using the stem as a holder, releasing the vascular aid from the T-shaped element to allow the vascular aid to remain within the two vessels, releasing the L-shaped elements from each other, and retracting the L-shaped elements from the vessels.

\* \* \* \* \*